United States Patent
Naiki

(10) Patent No.: US 6,238,665 B1
(45) Date of Patent: May 29, 2001

(54) ANTI-EDEMA AGENT

(75) Inventor: Mitsuru Naiki, Katoh-gun (JP)

(73) Assignee: Nippon Zoki Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/434,495

(22) Filed: Nov. 5, 1999

(30) Foreign Application Priority Data

Nov. 13, 1998 (JP) .................................................. 10-324012

(51) Int. Cl.[7] .................................................. A61K 39/395

(52) U.S. Cl. .............................. 424/130.1; 514/2; 514/21

(58) Field of Search .............................. 424/130.1, 133.1; 514/2, 21

(56) References Cited

U.S. PATENT DOCUMENTS

| 3,873,697 | 3/1975 | Filipp et al. |
| 4,704,273 | 11/1987 | McMichael. |
| 4,705,685 | 11/1987 | McMichael. |
| 4,705,687 | 11/1987 | Lau. |
| 4,812,449 | 3/1989 | Rideout. |
| 5,112,738 | 5/1992 | Buckler et al. |
| 5,354,848 | 10/1994 | Faligiani et al. |
| 5,622,970 | 4/1997 | Armistead et al. |
| 5,639,758 | 6/1997 | Sharpe et al. |
| 5,780,026 * | 7/1998 | Yoshii et al. .................. 424/130.1 |

FOREIGN PATENT DOCUMENTS

| 196 34 537 | 3/1998 | (DE). |
| 0 758 656 A2 | 2/1967 | (EP). |
| 0 646 376 A1 | 4/1995 | (EP). |
| 0 864 323 | 9/1998 | (EP). |

OTHER PUBLICATIONS

Naiki M. et al., "Rat Gamma Globulin/Hisstamine Inhibits Experimental Allergic Encephalomyelitis (EAE) In Lewis Rats," *International Congress of Immunology Abstracts*, Jul. 23, 1995, XP000672330.

Yoshii H. et al., "A complex of histamine mouse gamma-globulin preferentially inhibits allergen-induced peritoneal accumulation of eosinophils, but not neutrophils, in mice," *Journal of Allergy and Clinical Immunology*, (Dec. 1997) 100 (6 PT 1), 809–16, XP000876581.

Kagoshima, M. et al., *Inflamm. res.*, vol. 46, pp. 147–153 (1997).

Elwany, Samy et al., *The Journal of Laryngology and Otology*, vol. 111, pp. 935–940 (Oct., 1997).

Pop, S. et al., "Follow–up of the THG therapeutic action" Chemical Abstracts Service No. 89–140377 HCA XP002130193. Farmacia (Bucharest) (1978), 26 (1), pp. 9–12.

M. Naiki et al., "Neurotropin Inhibits Experimental Allergic Encephalomyelitis (EAE) In Lewis Rats", *Int. J. Immunopharmac.*, 13(2/3), 235–243 (1991).

"Drug Evaluations Annual 1995", American Medical Association, pp. 438–445 (1995).

(List continued on next page.)

Primary Examiner—Anthony C. Caputa
Assistant Examiner—Karen Canella
(74) Attorney, Agent, or Firm—Hollander Law Firm, P.L.C.

(57) ABSTRACT

A pharmaceutical composition comprising a pharmaceutically effective amount of histamine-added immunoglobulin substantially suppresses edema formation and an increase of vascular permeability of the blood-brain barrier. The histamine-added immunoglobulin may be administered with a high degree of safety and a low incidence of side effects. The histamine-added immunoglobulin and pharmaceutical compositions containing it may be used for treatment and prevention of edema, edema formation, and an increase of vascular permeability of the blood-brain barrier.

20 Claims, 2 Drawing Sheets

OTHER PUBLICATIONS

Goodin, "The use of immunosuppressive agents in the treatment of multiple sclerosis: A critical review", *Neurology,* vol. 41, pp. 980–985 (1991).
Higashiguchi, et al., Chemical Abstracts 112:111828b, 1990.
Getlik, et al., Chemical Abstracts 67, #5, 20482v, 1967.
Volokhovskaya, et al., Chemical Abstracts, 115:21847q, 1991.
Yoshii, et al., "Inhibitory Effect of Histamine–Added Mouse γ–Globulin On Eosinophil Accumulation Induced By Allergen In Balb/c Mice", *Japanese Journal of Allergology,* 44:567–570 (1995).
Yoshii, et al., "A New Assay System Detecting Antibody Production And Delayed–Type Hypersensitivity Responses To Trinitrophenyl Hapten In An Individual Mouse", *Int. J. Immunopharmac.,* vol. 18, No. 1, pp. 31–36, 1996.
Fujiwara, et al., "Sandwich enzyme immunoassay of tumor–associated antigen sialosylated Lewis using β–D–galactosidase coupled to a monoclonal antibody of IgM isotype", *Journal of Immunological Methods,* 112, pp. 77–83, 1988.
Burnham, "Polymers for delivering peptides and proteins", *Am J Hosp Pharm,* vol. 51, pp. 210–218, Jan. 15, 1994.
Wood, et al., Biochemistry A Problems Approach, 2nd edition, pp. 155–156, 1981.
Naiki, et al., 9th International Congress of Immunology, p. 183, abstract 1084, Jul. 23–29, 1995.
Kaneko, et al., "Role of Interleukin–5 in Local Accumulation of Eosinophils in Mouse Allergic Peritonitis," *Int. Arch Allergy Appl Immunol.,* 1991; 96: 41–45.
Kaplan A.P., *Allergy,* second edition, 1977, pp. 148–178, 260–261, 426–427, 439–440, 456–457, 482–483, 554, 597–598, 861–875.
Roitt, I. et al, "Hpersensitivity—Type IV", *Immunology,* 2nd ed., 1989, pp. 22.1–22.10.
Dunn, C. J., et al., "Murine Delayed–Type Hypersensitivity Granuloma: An Improved Model For The Identification And Evaluation Of Different Classes Of Anti–Arthritic Drugs," *Int. J. Immunopharmac.,* vol. 12, No. 8, pp. 899–904, 1990.
Yu, M., et al., "Interferon–β inhibits progression of relapsing–remitting experimental autoimmune encephalomyelitis," *Journal of Neuroimmunology* 64 (1996), pp. 91–100.
Arnason, "Interferon Beta in Multiple Sclerosis," *Clinical Immunology and Immunopathology,* vol. 81, No. 1, Oct., pp. 1–11, 1996.
The Merck Index, Twelfth Edition, 1996, p. 807.
*Sigma Biochemicals Organic Compounds for Research and Diagnostic Reagents,* 1995, pp. 470–472, and 1365–1368.
Curtis, et al., *Biology,* Fifth edition, Worth Publishers (New York), 1989, pp. 835–836.
Atton–Chamla et al., "Premenstrual syndrome and atopy: a double–blind clinical evaluation of treatment with a gamma–globulin/histamine complex," *Pharmatherapeutica,* vol. 2, No. 7, 1980, pp. 481–486.
Tanizaki et al., "Inhibitory Effect of Histamine–Gamma Globulin Conjugate on IgE–Mediated Reactivity of Human Basophils," *Jpn. J. Allergol.* 33, (12), pp. 1025–1029, 1984.
Peacock, Jr., E. E., *Wound Repair,* Third Edition, W. B. Saunders Co., 1984, pp. 96–97.
Fahey et al., "Status of Immune–based therapies in HIV infection and AIDS," *Clin. exp. Immunol.* (1992) 88, 1–5.
*Fundamental Immunology,* Third Edition, W. E. Paul, Editor, Raven Press, 1993, pp. 1354–1369.

\* cited by examiner

ANTI-EDEMA AGENT

FIELD OF THE INVENTION

The present invention relates to suppression of edema formation and suppression against an increase of vascular permeability of the blood-brain barrier using an anti-edema agent containing histamine-added immunoglobulin as an effective component.

BACKGROUND OF THE INVENTION

A complex of immunoglobulin and histamine has been known as a drug preparation, histamine-added immunoglobulin. It restores histamine fixing ability which is lowered in patients suffering from allergy and asthma. Accordingly, histamine-added immunoglobulin is used as an agent for nonspecific hyposensitizing therapy for bronchial asthma, allergic rhinitis, vasomotor rhinitis and allergic skin diseases such as urticaria, chronic eczema, atopic dermatitis, etc. Histamine-added immunoglobulin also exhibits suppressive action to liberation of histamine. It does not exhibit side effects exhibited by antihistamines and adrenocortical hormones used as symptomatic remedies. It has therefore been widely used as a pharmaceutical agent with high safety. See pages 463 and 464 of "Drugs in Japan, Ethical Drugs," edited by Japan Pharmaceutical Information Center; published by Yakugyo Jiho Co., Ltd., Japan in October 1996.

In addition to said medical indications, it has been reported that histamine-added immunoglobulin has a suppressive action against hypereosinophilicity, immunomodulating action and the like, and the oral administration of histamine-added immunoglobulin expresses the same pharmacological activity as shown by usual hypodermic injection. See, for example, Japanese Laid-Open Patent Publications Hei-7/53406, and Hei-9/31311. However, there has been no report regarding a suppressive action against edema formation and a suppressive action against an increase of vascular permeability of the blood-brain barrier which is exhibited by histamine-added immunoglobulin.

The present inventor has conducted an extensive investigation on histamine-added immunoglobulin and found that it also has a suppressive action against edema and a suppressive action against an increase of vascular permeability of the blood-brain barrier. The present invention provides an anti-edema agent, a suppressive agent against edema formation, and a suppressive agent against an increase of vascular permeability of the blood-brain barrier containing histamine-added immunoglobulin as an effective component. The anti-edema and suppressive agents have a high degree of safety with little side effects.

SUMMARY OF THE INVENTION

Edema, edema formation, and an increase of vascular permeability of the blood-brain barrier are substantially suppressed by administering to a patient in need of such treatment a pharmaceutical composition comprising a pharmaceutically effective amount of a histamine-added immunoglobulin and a pharmaceutically acceptable carrier. The histamine-added immunoglobulin may be prepared by dissolving about 1 mg to about 200 mg, preferably about 5 mg to about 50 mg, of immunoglobulin and about 0.01 $\mu$g to about 2 $\mu$g, preferably about 0.05 $\mu$g to about 0.5 $\mu$g, of a histamine component in a pharmaceutically acceptable solution.

DETAILED DESCRIPTION OF THE INVENTION

Figure 1:
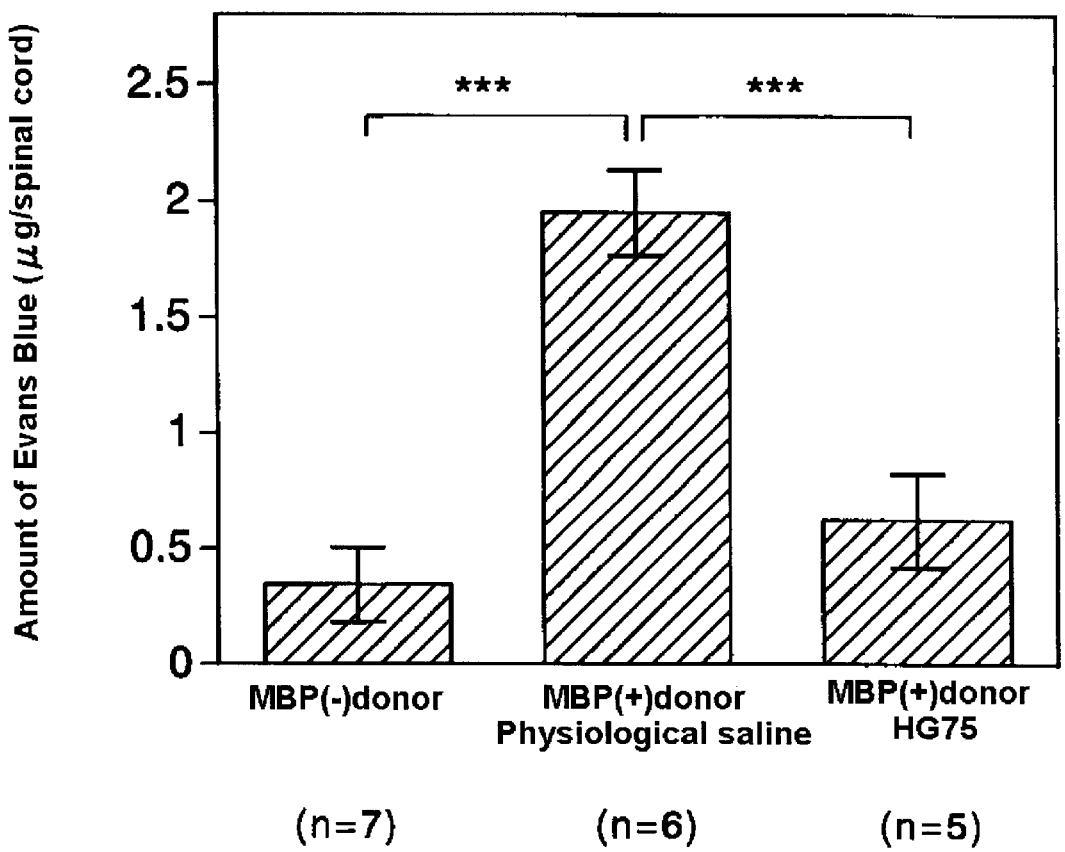
FIG. 1 is a graph showing an example of suppressive action against an increase of vascular permeability of the blood-brain barrier accompanying EAE which is achieved by administration of histamine-added immunoglobulin in accordance with the present invention.

In accordance with the present invention a pharmaceutically effective amount of histamine-added immunoglobulin may be administered to a patient in need of treatment for or in need of prevention of edema, edema formation, or an increase of vascular permeability of the blood-brain barrier.

Histamine-added immunoglobulin, which is an effective component of the pharmaceutical composition of the present invention, is a complex of immunoglobulin and histamine. The histamine-added immunoglobulin can be prepared by mixing of an immunoglobulin component with a histamine component to obtain a substantially homogeneous mixture. In the case of a pharmaceutical composition which is used for treatment of a human being, it goes without saying that human immunoglobulin may be used as a material to prepare the complex. The human immunoglobulin can be obtained from serum or placenta plasma by conventional methods. In order to secure safety as a pharmaceutical agent, the standards which are usually stipulated for plasma fraction preparations should be satisfied. For example, human plasma which is negative to HBs antigen, HCV antibody and HIV antibody is used and is further subjected to a heating treatment to avoid the danger of contamination with hepatitis virus and AIDS virus. The heat treatment which is commonly used for inactivation of virus may be used to treat plasma for use in preparing the immunoglobulin. For example, a liquid phase heat treatment at 60° C. for 10 hours, a steam-heat treatment at 60° C. for 10 hours, a dry-heat treatment at 65° C. for 96 hours, etc. are usually conducted for fractionated plasma preparations and may be employed to heat treat the immunoglobulin or its source herein.

In the case of application to animals other than human beings, immunoglobulin may be prepared from an animal other than a human being depending upon the species of the animal to be treated. For example, if a mouse is to be treated, a mouse immunoglobulin may be prepared for combining with the histamine component.

Immunoglobulin has various classes such as IgG, IgA, IgM, etc. For the immunoglobulin of the present invention, each class or type of immunoglobulin may be employed either solely or jointly together. In embodiments of the invention, the immunoglobulin which is employed may be a commercially available animal or human γ-globulin fraction of serum proteins, or one or more purified immunoglobulins such as animal or human IgG, IgA, or IgM which are disclosed, for example, in the 1995 Sigma Chemical Co. Catalog of "Biochemical Organic Compounds for Research and Diagnostic Reagents," Sigma Chemical Company, St. Louis, Mo., pp 470–472, and 1365–1368 (1995), herein incorporated by reference.

Free histamine and its pharmaceutically acceptable salts such as hydrochloride, phosphate and picrate salts may be used alone or in combination as a histamine component. A preferred histamine component which may be employed is histamine dihydrochloride.

In the manufacture of the pharmaceutical agent of the present invention, it can be prepared, for example, by dissolving about 1 mg to about 200 mg, preferably about 5 mg to about 50 mg, of immunoglobulin and about 0.01 µg to about 2 µg, preferably about 0.05 µg to about 0.5 µg, of a histamine component in a suitable pharmaceutically acceptable solution such as physiological saline solution, distilled water, etc. with conventional means, mixing and stirring. The histamine-added immunoglobulin may be stored in frozen or freeze-dried form.

Histamine-added immunoglobulin of the present invention can be made into pharmaceutical preparations by combining a pharmaceutically effective amount of the histamine-added immunoglobulin with at least one pharmaceutically acceptable carrier or diluent. It can be made into various types of preparations by known methods. The histamine-added immunoglobulin may be made into solid, semisolid, liquid or aerosol formulations for oral or parenteral administration. The histamine-added immunoglobulin of the present invention can be used either solely or jointly together in pharmaceutically effective amounts with pharmaceutically effective amounts of other pharmaceutically active components for treating animals or humans.

In the case of injections, it is preferable to prepare the pharmaceutical composition as an isotonic solution using distilled water for injection or physiological saline solution. In its manufacture, additives such as auxiliary solubilizers, isotonizing agents, stabilizers, buffers, preservatives, etc. may be used in addition to histamine-added immunoglobulin. Examples of the applicable additives are citric acid, sodium benzoate, glycine, sodium sulfite, sodium bisulfite, sodium pyrosulfite, sodium thiosulfate, cysteine hydrochloride, phosphates, sodium ascorbate, sodium chloride, sodium bicarbonate, etc. Further, the pharmaceutical agent of the present invention may be prepared as an injectable preparation which is dissolved upon actual use. Thus, the agent may be prepared in a dry state or a solution may be filled in vials or the like followed by freeze-drying. In the manufacture of the dry preparation for injection, fillers such as glucose, mannitol and sorbitol may, if necessary, be added in addition to the above mentioned additives.

In the case of preparations for oral administration, histamine-added immunoglobulin of the present invention solely or together with commonly used pharmaceutically acceptable excipients in pharmaceutically acceptable amounts such as at least one pharmaceutically acceptable additive or carrier (e.g. lactose, mannitol, corn starch, potato starch, etc.) may be mixed with one or more pharmaceutically acceptable: (1) binders such as crystalline cellulose, cellulose derivatives, gum arabicum, corn starch, gelatin, etc., (2) disintegrating agents such as corn starch, potato starch, potassium carboxymethylcellulose, etc., 3) lubricating agents such as talc, magnesium stearate, etc. and 4) other pharmaceutically acceptable excipients including pharmaceutically acceptable bulking agents, moisturizing agents, buffers, preservatives, perfumes and the like to obtain tablets, diluted powders, granules or capsules.

It is also possible, depending upon the type of the disease or the condition of the patient to prepare pharmaceutical preparations other than the above-mentioned ones which are suitable for therapy. Exemplary of other pharmaceutical preparations are inhalations, aerosol preparations, ointments, collyriums, suppositories, etc.

The preferred dosage of histamine-added immunoglobulin of the present invention may vary depending upon the type of the disease, the condition of the patient, age or sex of the patient, form of the preparation, method for the administration, term for the administration, etc. To achieve a desired effect, about 1 mg to about 300 mg, preferably about 5 mg to about 150 mg may be usually given to common adults once or several times a week by hypodermic injection, although the present invention is not particularly limited to such dosage.

Preferred embodiments of the present invention are:

(1) An anti-edema agent containing histamine-added immunoglobulin as an effective component.

(2) A suppressive agent against edema containing histamine-added immunoglobulin as an effective component.

(3) A suppressive agent against an increase of vascular permeability of the blood-brain barrier containing histamine-added immunoglobulin as an effective component.

(4) An agent according to any of the above paragraphs (1) to (3), in which the ratio of immunoglobulin to histamine component is 1 mg to 200 mg of immunoglobulin component to 0.01 µg to 2 µg of histamine component.

(5) An agent according to any of the above paragraphs (1) to (3), in which the ratio of immunoglobulin to histamine component is 5 mg to 50 mg of immunoglobulin component to 0.05 µg to 0.5 µg histamine component.

(6) An agent according to any of the above paragraphs (1) to (5), in which the ratio of immunoglobulin to histamine component is 12.0 mg of immunoglobulin component to 0.15 µg histamine component.

(7) An agent according to any of the above paragraphs (1) to (6), in which the immunoglobulin component is human immunoglobulin.

(8) An agent according to any of the above paragraphs (1) to (7), in which the histamine component is histamine dihydrochloride.

(9) An agent according to any of the above paragraphs (1) to (8) formulated as an injectable preparation.

The present invention is further illustrated in detail by way of the following non-limiting examples wherein all parts, percentages and ratios are by weight, all temperatures are in °C., and all reactions are conducted at about atmospheric pressure unless indicated to the contrary:

EXAMPLE

In this example, the preparation of histamine-added immunoglobulin of the present invention and its pharmacological activity is illustrated. Rats were used as experimental animals in the following pharmacological tests and, accordingly, rat immunoglobulin was used in place of human immunoglobulin. Both types of histamine-added immunoglobulin may be produced in the same manner. Thus, for the pharmacological tests on rats, rat immunoglobulin and histamine dihydrochloride were dissolved in physiological saline solution using the following mixing ratios, stirred at room temperature for 2 hours, freeze-dried and upon use, dissolved by adding a physiological saline solution thereto for hypodermic administration:

| Product of the present invention | Amount of rat immunoglobulin | Amount of histamine.2HCl |
|---|---|---|
| HG50 | 5.3 mg | 0.10 µg |
| HG75 | 12.0 mg | 0.15 µg |
| HG90 | 28.8 mg | 0.30 µg |

Each of the HG50, HG75 and HG90 products prepared above exhibited significant effects in all of the following pharmacological tests and, accordingly, only the results obtained for HG75 are given as representative thereof.

THE PHARMACOLOGICAL TESTS

The pharmacological tests were carried out as follows:

1) Animals

Lewis rats (6–10 weeks old, female, SPF) were purchased from Charles River, Japan. Rats were preliminarily maintained for 5 days in an animal room (22°±2° C. room temperature and 55±10% humidity) with artificial lighting for 12 hours from 8 a.m. to 8 p.m., and then healthy and normal rats were utilized for experiments.

2) Preparation and Administration of Histamine-added Rat Immunoglobulin

Rat immunoglobulin prepared from normal rat serum (Cohn fractions II and III) and histamine dihydrochloride were dissolved in physiological saline in final concentrations of 26.6 mg/mL and 0.333 µg/mL respectively. The mixture was stirred for 2 hours and then utilized as HG75. HG75 was injected subcutaneously into the back of each rat on every second day from the immunizing day or cell-transferring day. To a control rat, physiological saline was injected in the same manner as HG75.

3) Method for Inducing Passive Experimental Allergic Encephalomyelitis (pEAE)

A solution (400 µg/mL) of guinea pig myelin basic protein (GB-MBP 68–84) including synthetic peptide (MBP 68–84) corresponding to the encephalitogenic determinants was mixed with an equal volume of complete adjuvant (H37Ra) to give an emulsion. The emulsion (0.1 mL) was subcutaneously administered to the left hind foot pad of Lewis rats anesthetized with diethylether. The spleen cells were isolated from the rats 10–14 days after the immunization and the cell suspension was prepared. Erythrocytes were removed by using a solution of 0.75% ammonium chloride and 17 mM Tris-HCl (pH=7.65). After centrifugation, the spleen cells were suspended in RPMI-1640 medium and viable cells were counted by using 0.4% trypan blue solution. The cells were suspended at a concentration of $2 \times 10^6$ cells/mL in a medium (RPMI-1640 containing 10 mM HEPES, 20 mM glutamine, 50 µg/mL penicillin, 50 U/mL streptomycin and $5 \times 10^{-5}$ M 2-mercaptoethanol) supplemented with 7% fetal calf serum. The cells ($2 \times 10^7$ cells/10 mL) were cultured in a culture dish at 37° C. in an atmosphere of 5% $CO_2$ and 95% air in the presence of 2 µg/mL Concanavalin A. Cultured cells were collected and washed 3 times by centrifugation. The aggregated cells were removed by filtration, and the cell concentration was determined by using 0.4% trypan blue. The cell concentration was adjust to $4 \times 10^7$ cells/mL with physiological saline. Each Lewis rat was irradiated with 800 rad X-ray by an X-ray irradiator (MBR-1520R, Hitachi, Japan) and then the cells ($2 \times 10^7$ cells/0.5 mL) were transferred intravenously into the tail vein of the rat.

4) Clinical Assessment of EAE

The clinical signs of the disease on tested rats were assessed by using a clinical index to grade animals on indexes from 0 to 5 as follows. When the clinical sign of a grade from 2 to 5 appeared partially, the value by subtracting 0.5 from each grade was adopted. The clinical signs were assessed by a blind method, namely, the treatment of a rat such as with or without a test drug was not clarified for the operator.

| Grade | Clinical Sign |
|---|---|
| 0 | Normal |
| 0.5 | Slight tail weakness |
| 0.75 | Moderate tail weakness |
| 1 | Disappearance of ability to hold tail up |
| 2 | Inactive |
| 3 | Paralysis of one hind leg |
| 4 | Paralysis of both hind legs |
| 5 | Paralysis of both hind legs accompanied by urinary incontinence |

5) Measurement of Vascular Permeability and Edema

At a settled day after cell transfer, 2% Evans blue solution (diluted with saline) was intravenously injected into rats (1 mL per 100 g body weight). Two hours later, rats were perfused with 250 mL saline and then their spinal cords were isolated. The wet weight of the isolated spinal cords was measured. The spinal cords were dried at 90° C. for 24 hours and the dry weight was measured. The water content was determined by deducting the dry weight from the wet weight.

To determine the amount of Evans blue infiltrated into the central nervous system, 0.5 mL of 1N potassium hydroxide was added to spinal cord tissues and cultured at 37° C. for 18 hours after being well stirred. In addition, 4.5 mL of 0.6N phosphoric acid-acetone buffer (5:13) was added into the mixture and well stirred again. After removal of precipitate from the mixture by filtration, absorbance (OD: 620 nm) of the filtered solution was measured. The standard solution of various concentrations added with from 0.3125 µg to 10 µg of Evans blue were prepared to obtain the standard curve, and the amount of Evans blue in each sample was calculated from the standard curve.

6) Statistical Analysis

The amounts of Evans blue in the spinal cords and water contents were shown as mean±S.E., and were analyzed with the Scheffe test (multiple comparison method) to obtain the significant difference compared to the control. The results are shown as below.

7) Progress of Changes of Vascular Permeability Accompanying EAE

To clarify the participation of an increase of vascular permeability of the blood-brain barrier (BBB) in the onset of EAE, Evans blue was administered intravenously from the cell transferred date and the amount of Evans blue infiltrated into spinal cords within a settled time was measured. In the rats on the 3rd day after cell transfer (average clinical score: 0), the amount of Evans blue infiltrated into spinal cords was not different from the amount for the control group (rats without cell transfer). On the 4th day after cell transfer (average clinical score: 0.7), the onset of EAE can be observed and the amount of Evans blue infiltrated into spinal cords increased significantly ($p<0.05$) compared with the amount for the control group. On the 5th day after cell transfer (average clinical score: 3.0), the amount of Evans blue infiltrated into spinal cords was the same level as observed on the 4th day and increased significantly ($p<0.05$) compared with the amount for the control group. However, no significant difference in the amount of Evans blue compared to the amount for the control group was observed on the 7th day (average clinical score: 1.0) in which the onset of EAE was decreased and on the 11th day in which the appearance of EAE disappeared.

8) Suppressive Effect of the Agent of the Present Invention on Increase of Vascular Permeability Accompanying EAE It was suggested that vascular permeability had some relationship with onset of pEAE, because the increase of vascular permeability of BBB was observed prior to the appearance of EAE. To study the effects of the present pharmaceutical agent on increase of vascular permeability, HG75 (150 mg/kg) was administered subcutaneously to the back of each rat 3 times, every other day from the cell transferred dote. To the rats 5 days after the cell transfer, 2% of Evans blue solution was administered intravenously (0.1 mL/100 g). Two hours later, hemoperfusion from the rat heart using 400 mL of saline was conducted to remove Evans blue from the peripheral blood. The whole spinal cords were isolated and the amount of infiltrated Evans blue was measured. An example of the results is shown in FIG. 1. As indicated in FIG. 1, the amount of Evans blue in the EAE inducted rats was increased to about 6 times compared to the amount of Evans blue in the EAE non-inducted rats (a group without administration of MBP) and a significant difference ($p<0.001$) was observed. On the other hand, the amount of Evans blue in the rats to which the agent of the present invention was administered was the same level as the amount in the EAE non-inducted rats and a significant suppressive effect ($p<0.001$) was observed as compared to the amount for the control EAE rats.

Figure 2:
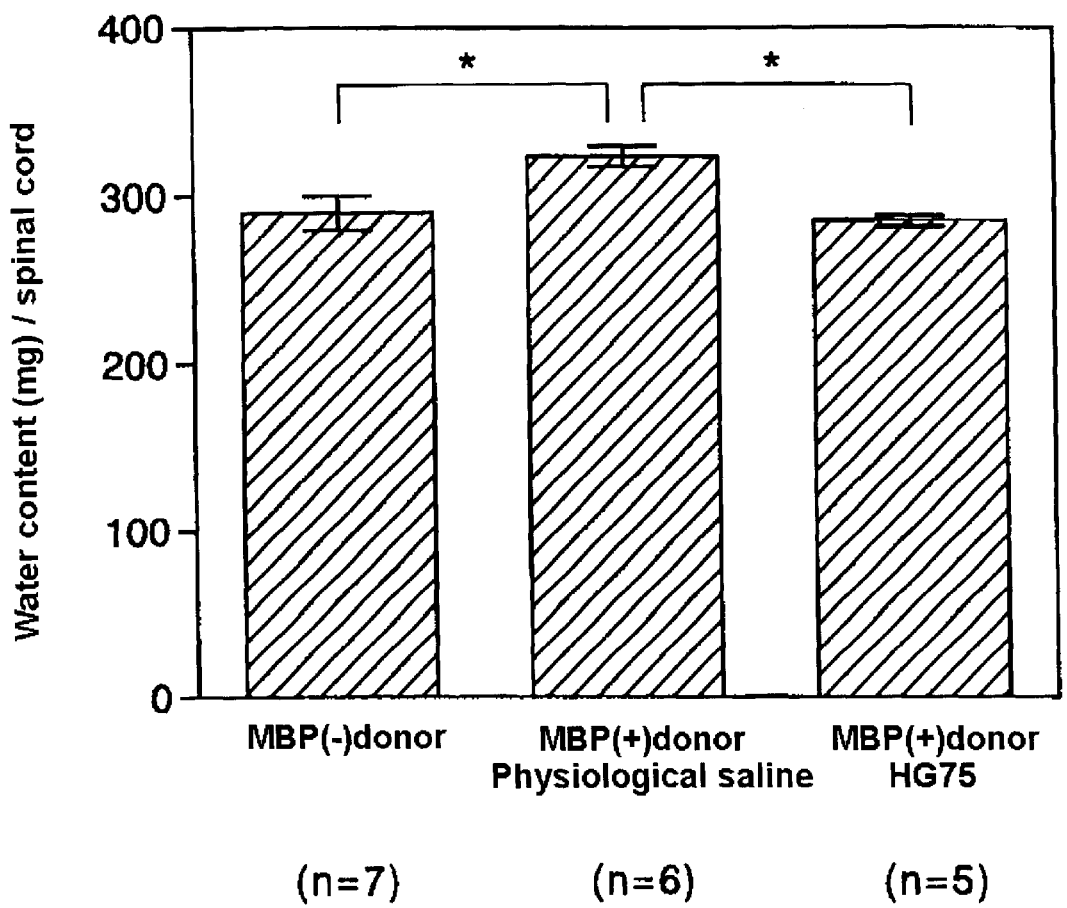
FIG. 2 is a graph showing an example of suppressive action against edema formation accompanying EAE which is achieved by administration of histamine-added immunoglobulin in accordance with the present invention.

9) Suppressive Effect of the Agent of this Invention on Edema Formation Accompanying EAE On the 5th day from the cell transferred date, the spinal cords were isolated and dried for 24 hours. Water content was calculated by deducting the dry weight of the spinal cords from the wet weight of the spinal cords. We studied the effect of the agent of this invention (150 mg/kg) by evaluation using said water content as an index. An example of the results is shown in FIG. 2. As indicated in FIG. 2, the water content in the spinal cords of the EAE inducted rats was significantly increased ($p<0.05$) compared with the water content for the EAE non-inducted rats. On the other hand, the water content in the spinal cords of the rats administered with the present pharmaceutical agent was decreased to the same level as the spinal cord water content for the EAE non-inducted rats and a significant decrease ($p<0.05$) was observed as compared to the spinal cord water content for the control EAE rats.

As shown in FIG. 1, the pharmaceutical agent of the present invention has a suppressive action against an increase of vascular permeability of the blood-brain barrier. It is also apparent from the results shown in FIG. 2, that the agent of this invention has a suppressive action against edema formation. In the earliest stage of the formation of demyelination, it has been suggested that abnormality of the blood-brain barrier is important. It has been clarified that the blood-brain barrier attaches primary importance to cerebrovascular endothelial cells in the central nervous system. In the normal state, the blood-brain barrier has very close conjugations and the number of small holes on the endothelial cells is very small. According to such particular structure of the endothelial cells which is different from the structure of other regions, the transfer of substances in the blood vessels to cerebral parenchyma is protected by the blood-brain barrier. However, in edema regions, an acute increase of vascular permeability of endothelium is observed. Therefore, the agent of the present invention is very useful as a suppressive agent against an increase of vascular permeability of the blood-brain barrier, an anti-edema agent, and a suppressive agent against edema formation.

Histamine-added immunoglobulin, which is an active component of the agent of the present invention, has a low incidence of side effects. Therefore, the agent of the present invention is very useful as an anti-edema agent, a suppressive agent against edema formation and a suppressive agent against an increase of vascular permeability of the blood-brain barrier having high safety.

In embodiments of the invention, edema, edema formation, or diseases or conditions which cause an increase of vascular permeability of the blood-brain barrier may be treated or prevented in a patient in need of such treatment or prevention by qualitatively or quantitatively measuring edema, edema formation or an increase of vascular permeability of the blood-brain barrier, such as by measuring or monitoring Evans blue infiltration or an increase in water content, determining whether edema or vascular permeability of the blood-brain barrier are present at an abnormal level, and administering the histamine-added immunoglobulin to suppress edema or an increase in vascular permeability of the blood-brain barrier to normal levels so as to alleviate symptoms of the disease or condition.

Accordingly, histamine-added immunoglobulin may be employed in accordance with the present invention for the treatment of diseases or conditions other than allergies, asthma, and autoimmune diseases such as rheumatoid arthritis.

What is claimed is:

1. A method for treating brain edema or an increase in permeability of the blood-brain barrier comprising administering to a patient known to be in need of such treatment a pharmaceutical composition comprising a pharmaceutically effective amount of histamine-added immunoglobulin.

2. A method as claimed in claim 1 wherein said histamine-added immunoglobulin is administered as an injectable preparation.

3. A method as claimed in claim 1 wherein said histamine-added immunoglobulin is obtained by admixing an immunoglobulin component and a histamine component in a weight ratio of about 1 mg to about 200 mg of the immunoglobulin component to about 0.01 µg to about 2 µg of the histamine component.

4. A method as claimed in claim 3 wherein said weight ratio is about 5 mg to about 50 mg of the immunoglobulin component to about 0.05 µg to about 0.5 µg of the histamine component.

5. A method as claimed in claim 3 wherein said immunoglobulin component is human immunoglobulin.

6. A method as claimed in claim 3 wherein said histamine component is at least one pharmaceutically acceptable histamine salt.

7. A method as claimed in claim 6 wherein said salt is histamine dihydrochloride.

8. A method for the treatment of brain edema or edema formation comprising determining the presence of edema, and administering to a patient in need of such treatment a pharmaceutically effective amount of a histamine-added immunoglobulin to substantially suppress edema formation.

9. A method as claimed in claim 8 wherein said histamine-added immunoglobulin is administered as an injectable preparation.

10. A method as claimed in claim 8 wherein said histamine-added immunoglobulin is obtained by admixing an immunoglobulin component and a histamine component in a weight ratio of about 1 mg to about 200 mg of the immunoglobulin component to about 0.01 µg to about 2 µg of the histamine component.

11. A method as claimed in claim 10 wherein said weight ratio is about 5 mg to about 50 mg of the immunoglobulin component to about 0.05 µg to about 0.5 µg of the histamine component.

12. A method as claimed in claim 10 wherein said immunoglobulin component is human immunoglobulin.

13. A method as claimed in claim 10 wherein said histamine component is at least one pharmaceutically acceptable histamine salt.

14. A method as claimed in claim 13 wherein said salt is histamine dihydrochloride.

15. A method for the suppression of an increase in permeability of the blood-brain barrier comprising determining an increase in permeability of the blood-brain barrier, and administering to a patient in need of such treatment a pharmaceutically effective amount of a histamine-added immunoglobulin to substantially suppress permeability of the blood-brain barrier.

16. A method as claimed in claim 15 wherein said histamine-added immunoglobulin is obtained by admixing an immunoglobulin component and a histamine component in a weight ratio of about 1 mg to about 200 mg of the immunoglobulin component to about 0.01 $\mu$g to about 2 $\mu$g of the histamine component.

17. A method for treating brain edema or a disease or condition where an increase in permeability of the blood-brain barrier is symptomatic comprising administering to a patient known to be in need of such treatment a pharmaceutical composition consisting essentially of a pharmaceutically effective amount of histamine-added immunoglobulin, and a pharmaceutically acceptable carrier.

18. A method as claimed in claim 17 wherein said patient is in need of treatment for brain edema.

19. A method as claimed in claim 17 wherein said histamine-added immunoglobulin is obtained by admixing an immunoglobulin component and a histamine component in a weight ratio of about 1 mg to about 200 mg of the immunoglobulin component to about 0.01 $\mu$g to about 2 $\mu$g of the histamine component.

20. A method as claimed in claim 19 wherein said weight ratio is about 5 mg to about 50 mg of the immunoglobulin component to about 0.05 $\mu$g to about 0.5 $\mu$g of the histamine component, said immunoglobulin component is human immunoglobulin, and said histamine component is histamine dihydrochloride.

* * * * *